United States Patent [19]

Kojima et al.

[11] 4,334,021

[45] Jun. 8, 1982

[54] PROCESS FOR PRODUCING COPROPORPHYRIN III

[75] Inventors: Ichiro Kojima, Yokosuka; Kenji Maruhashi, Yokohama; Yasuo Fujiwara, Tokyo, all of Japan

[73] Assignee: Nippon Oil Company, Ltd., Tokyo, Japan

[21] Appl. No.: 211,057

[22] Filed: Nov. 28, 1980

[30] Foreign Application Priority Data

Nov. 29, 1979 [JP] Japan .............................. 54/153648

[51] Int. Cl.$^3$ .............................................. C12P 17/16
[52] U.S. Cl. .................................... 435/118; 435/830
[58] Field of Search ................................ 435/118, 119

[56] References Cited

U.S. PATENT DOCUMENTS 3,902,967 9/1975 Chibata et al. ...................... 435/172
4,115,197 9/1978 Queener .............................. 435/172

OTHER PUBLICATIONS

Biochemical Journal, vol. 62, pp. 78-93, (1956).
Hoppe-Seyler's Zeitschrift for Physiological Chemistry, vol. 354 (8), p. 841, (1973).

Primary Examiner—Lionel M. Shapiro
Attorney, Agent, or Firm—Wenderoth, Lind & Ponack

[57] ABSTRACT

In a process for producing coproporphyrin III which comprises cultivating a coproporphyrin III-producing microorganism of the genus Arthrobacter in a culture medium containing a carbon source, a nitrogen source and a mineral and recovering coproporphyrin III from the culture broth, the improvement wherein the culture medium contains at least 0.1 g, per liter of the culture medium, of L-cystine, at leas 0.5 g, per liter of the culture medium, of $Mg^{++}$, *or both; and coproporphyrin III-producing microoganisms.*

6 Claims, No Drawings

PROCESS FOR PRODUCING COPROPORPHYRIN III

It is known that protoporphyrin IX having a porphyrin structure is useful in pharmaceutical applications. The present invention relates to a process for producing coproporphyrin III which has a porphyrin structure and is useful in a wide range of applications such as pharmaceuticals, intermediates for pharmaceuticals or red dyes for drinks and foods.

More specifically, this invention relates to a process for producing coproporphyrin III which comprises cultivating a coproporphyrin III-producing microorganism belonging to the genus Arthrobacter in a culture medium containing a carbon source, a nitrogen source and a mineral and recovering coproporphyrin III from the resulting culture broth, characterized in that the culture medium contains at least 0.1 g, per liter of the culture medium, of L-cystine, at least 0.5 g, per liter of the culture medium, of $Mg^{++}$, or both.

Japanese Laid-Open Patent Publication No. 7492/77 discloses a process which comprises cultivating a microorganism capable of producing coproporphyrin III of the following formula

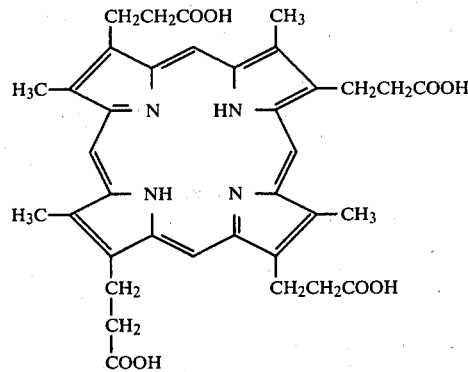

selected from microorganisms of the genera Arthrobacter and Brevibacterium, and recovering coproporphyrin III from the culture broth. According to this process, coproporphyrin III can be formed in a much higher yield than in processes involving the use of coproporphyrin III-producing microorganisms of other genera.

The present inventors made investigations in order to provide an improved process for producing coproporphyrin III in further improved yields. As a result, they have found that coproporphyrin III can be obtained in markedly improved yields with good reproducibility by performing the cultivation in a culture medium which contains a suitable amount, preferably at least 0.1 g per liter of the culture medium, of L-cystine which is not specifically described as an ingredient of the culture medium in the above-cited Japanese Laid-Open Patent Publication No. 7492/77.

It was also found that coproporphyrin III can be produced in a much improved yield with good reproducibility by performing the cultivation in a culture medium containing a compound capable of giving $Mg^{++}$, such as magnesium salts, exemplified as the inorganic salt in the above-cited Japanese Laid-Open Patent Publication No. 7492/77 in an amount not specifically disclosed in the above-cited patent document, particularly in an amount of at least 0.5 g per liter of the culture medium calculated as $Mg^{++}$.

They also found that it is possible to form mutants or varieties having the markedly improved ability to produce coproporphyrin III but having substantially the same microbiological properties as the parent strain dislcosed in the above-cited Japanese Laid-Open Patent Publication No. 7492/77, and that by cultivating such a mutant or variety in a culture medium containing the aforesaid L-cystine and/or $Mg^{++}$, coproporphyrin III can be produced in a much improved yield with better reproducibility as compared with the case of using the parent strain.

It is an object of this invention to provide an improved process for producing coproporphyrin III in an improved yield at low cost by an industrially easy operation.

The above and other objects and advantages of this invention will become apparent from the following description.

Specific examples of the coproporphyrin III-producing known strains of the genus Arthrobacter that can be used in this invention are shown below.

(1) *Arthrobacter hyalinus*

FERM-P NO. 3125 [Fermentation Research Institute, Agency of Industrial Science and Techlonogy, Japan (FRI, Japan)]; ATCC 31263 (American Type Culture Collection); DSM 867 (German Collection of Microorganisms; Deutsche Sammlung von MIkroorganismen).

(2) *Arthrobacter globiformis*

IFO 12137 (Institute for Fermentation, Osaka, Japan); ATCC 8010.

(3) *Arthrobacter aurescens*

IFO 12136; ATCC 13344.

(4) *Arthrobacter pascens*

IFO 12139; ATCC 14358.

(5) *Arthrobacter ramosus*

IFO 12958; ATCC 13727.

(6) *Arthrobacter cremeus*

FERM-P No. 3126.

(7) *Arthrobacter resinosus*

FERM-P No. 3131.

(8) *Arthrobacter isopropanolophila*

FERM-P No. 3129.

(9) *Arthrobacter flavidus*

FERM-P No. 3130.

The microbiological properties of the above known strains (1) and (6) to (9) are described in detail, for example, in Japanese Laid-Open Patent Publication No. 7492/77. The microbiological properties of the known strains (2), (3), (4) and (5) are described, for example, in Bergey's Manual of Determinative Bacteriology, 8th edition.

These known strains can be easily obtained from the above depositories.

In the process of this invention, not only these coproporphyrin III-producing strains of the genus Arthrobacter, but also their mutants or varieties can be used.

These varieties or mutants differ from the parent strains only in that they have increased ability to produce coproporphyrin III, and their microbiological properties are subsantially the same as those of the parent strains. These varieties or mutants can be easily produced from the above known and readily available parent strains by means known to those skilled in the art.

For example, such a variety or mutant can be obtained by a known mutating treatment, such as ultraviolet irradiation, Co[60] isotope irradiation, or treatment with a mutant-inducing agent such as N-methyl-N'-nitro-N-nitorosoguanidine. According to one embodiment, a parent strain in subjected to the above irradiation treatment or to treatment with the above mutant-inducing agent, and the treated strain is cultivated in a mineral-agar medium containing an agent capable of inhibiting production of coproporphyrin III. As required, the above irradiation treatment or the treatment with the mutant-inducing agent and the cultivation are repeated, and a strain having the increased ability to produce coproporphyrin III is recovered. The cultivation can be carried out under the same cultivation conditions (temperature, pH) as in the case of cultivating the parent strain. The above inhibitor may be known ones, such as coproporphyrin III, L-tryptophan and 5-methyl-DL-tryptophan.

Thus, the present invention also provides a process for producing a variety or mutant of a coproporphyrin III-producing microorganisms, which comprises subjecting a coproporphyrin III-producing microorganism of the genus Arthrobacter to irradiation or to treatment with a mutant-inducing agent, cultivating the treated microorganism in a culture medium containing a substance capable of inhibiting production of coproporphyrin III, and recovering a strain having the increased ability to produce coproporphyrin III from the culture broth.

Specific examples of such varieties or mutants are a 5-methyl-DL-tryptophan-resistant strain of *Arthrobacter hyalinus* NOC 11001 (FERM-P No. 5256, ATCC NO. 31736), a coproporphyrin III-resistant strain of *Arthrobacter hyalinus* NOC 11002 (FERM-P No. 5259, ATCC No. 31739), an L-tryptophan-resistant strain of *Arthrobacter globiformis* NOC 11004, (FERM-P NO. 5258, ATCC 31738) and an L-tryprophan-resistant strain of *Arthrobacter pascens* NOC 11003 (FERM-P NO. 5257, ATCC No. 31737).

According to the process of this invention, the above-exemplified coproporphyrin III-producing microorganism of the genus Arthrobacter is cultivated in a culture medium, and coproporphyrin III is recovered from the culture broth directly or indirectly.

The culture medium used in this invention contains a carbon source, a nitrogen source, a mineral source, vitamins, an antifoamer, etc. Examples of the carbon source are carbohydrates, alcohols, hydrocarbons and bran. Examples of the nitrogen source are corn steep liquor, yeast extract, meat extract, peptone, fish meal, ammonium salts, protein decomposition products, amino acids (especially L-cystine), nitrate salts and urea. Examples of the inorganic salts are phosphates, $Mg^{++}$-producing magnesium compounds such as magnesium salts, zinc salts, calcium salts, manganese salts, molybdenum salts and copper salts.

The composition of the culture medium can be suitably changed, and during the cultivation, the various ingredients mentioned above may be additionally supplied to the cuture medium. For example, when an alcohol is used as the carbon source, it may be additionally supplied to the culture medium when the concentration of the remaining alcohol decreases beyond a predetermined level, or it may be supplied around the time of initiation of coproporphyrin III production. This can increase the output of coproporphyrin III.

Favorable results are obtained when iron salts are absent in the culture medium.

In cultivating the coproporphyrin III-producing strain of the genus Arthrobacter exemplified hereinabove, at least 0.1 g, per liter of the culture medium, of L-cystine, and/or at least 0.5 g, per liter of the culture medium, of $Mg^{++}$, preferably 0.1 to 5 g of L-cystine and/or 0.5 to 10 g, more preferably 1 to 10 g, especially preferably 3 to 5 g, of $M^{++}$ are included in the culture medium.

By performing this improved process in accordance with this invention, coproporphyrin III can be produced in a markedly improved output which is at least about two times, and frequently about three times, as large as that disclosed specifically in the above-cited Japanese Laid-Open Patent Publication No. 7492/77.

The cultivation is carried out under aerobic conditions by shaking or aeration agitation, but it is preferred to flow air such that the amount of dissolved oxygen in the cultivation system is maintained at as low a level as possible. The cultivation temperature is generally about 20° to about 40° C., and the pH of the culture medium is maintained at about 4 to about 9.5. The cultivation time is usually about 2 to 30 days, and may be varied depending upon the other cultivation conditions.

Since coproporphyrin III builds up in an improved output in the resulting cultivation product, for example in the culture broth, it can be extracted in good yields from the cultivation product by, for example, using a suitable extractant such as ethyl acetate acidified with acetic acid in a customary manner. The extraction is usually carried out after the microbial cells and other solid materials have been separated from the cultivation product. The extractant is treated with HCl-methanol to methyl-esterify corproporphyrin, and if required, the ester is purified by column chromatography on an alumina column to recover coproporphyrin III in the form of methyl ester.

In the process of this invention, coproporphyrin III may also be recovered from the reaction product with a coproporphyrin III-forming substrate of the microbaial cells separated from the cultivation product, preferably the microbial cells separated from the cultivation product which is obtained by cultivating a coproporphyrin III-producing strain of the genus Arthrobacter under coproporphyrin III-producing conditions suitable for the growth of the microbial cells, or a crude enzyme extract from the microbial cells.

Examples of the coproporphyrin III-forming substrate are glycine, fumaric acid, α-ketoglutaric acid, succinic acid, δ-aminolevulinic acid, salts of these acids, and substances containing these compounds. Examples of the salts include sodium, potassium and ammonium salts. The crude enzyme extract can be obtained, for example, by crushing the microbial cells by grinding, destroying the microbial cells by ultrasonic treatment, destroying the microbial cells by using an abrupt difference in pressure, or by destroying the microbial cells using a cellular membrane dissolving enzyme.

The reaction of the microbial cells or the crude enzyme extract from the microbial cells with the coproporphyrin III-forming substrate is carried out, for example, by shaking or stirring the reaction mixture, or allowing it to stand, at a temperature of about 20° to 40° C. and at a pH of about 4 to about 9.5 for about 5 hours to about 5 days.

Separation of coproporphyrin III from the reaction product can be performed in the same way as in the case of recovering coproporphyrin III from the culture broth. Accordingly, in the present invintion, copropoprophyrin III can be obtained in a high yield from the culture broth either directly, or indirectly after a lapse of a certain time.

The coproporphyrin III in the culture broth was determined as follows. 0.5 ml of the culture broth or its dilution was extracted with 10 ml of 0.1 N acetate buffer (pH 4.7) and 10 ml of ethyl acetate. Coproporphyrin III extracted into the ethyl acetate layer was dissolved in 10 ml of 5% hydrochloric acid. The absorbance of the hydrochloric acid at 401.5 nm was measured. The concentration of coproporphyrin III in the cultivation product was determined from a separately prepared calibration curve.

The following Examples illustrate the present invention more specifically.

EXAMPLE 1

*Arthrobacter globiformis* (ATCC 8010) was inoculated into a test tube, 21 mm in outside diameter, containing 15 ml of a sterilized culture medium containing per liter of deionized pure water, 10 g of glucose, 1.0 g of yeast extract, 3.0 g of peptone, 3.0 g of ammonium nitrate, 0.4 g of monopotassium phosphate, 1.5 g of disodium phosphate, 5.0 g of magnesium sulfate, 10 mg of manganese sulfate, 10 mg of zinc sulfate, 200 $\mu$g of copper sulfate, 10 $\mu$g of molybedenum trioxide, 5.0 g of calcium carbonate and 0.2 g of L-cystine, and cultivated with shaking at 30° C. for 3 days. A 50% aqueous solution of glucose was added every 2 to 3 days thereafter, and 75 g in total of glucose was added per liter of the culture broth over a cultivation period of 15 days.

The concentration of coproporphyrin III accumulated in the culture broth at this time was 250 mg/liter.

EXAMPLE 2

The same cultivation as in Example 1 was performed for 15 days except that the culture medium did not contain the L-cystine. The concentration of copropor- phyrin III accumulated in the culture broth at this time was 132 mg/liter.

COMPARATIVE EXAMPLE 1

The same cultivation as in Example 1 was performed for 15 days except that the culture medium did not contain the L-cystine, and the amount of magnesium sulfate was reduced to 0.5 g per liter of the culture medium. The concentration of coproporphyrin III accumulated in the culture broth at this time was 91 mg/liter.

EXAMPLE 3

*Arthrobacter globiformis* (ATCC 8010) was inoculated into a 500 ml Erlenmeyer flask containing 250 ml of the same sterilized culture medium as used in Example 1, and cultivated under shaking at 30° C. for 3 days. A 50% aqueous solution of glucose was added every 3 to 4 days thereafter, and 54 g in total of glucose was added per liter of the cuture broth over the course of 18 days. At this time, the concentration of coproporphyrin III accumulated in the culture broth was 225 mg/liter.

Four liters of the resulting culture broth was centrifuged for 10 minutes at 10,000 G to remove insoluble materials such as the microbial cells. The pH of the supernatant liquid was adjusted to 3.6, and centrifuged for 10 minutes at 1,000 G in order to remove the precipitate. Methanol and sulfuric acid were added to the precipitate, and the mixture was allowed to stand overnight in a refrigerator and then extracted with dichloromethane. The dichloromethane layer was repeatedly washed with water until sulfuric acid was removed from it. The dichloromethane layer was then concentrated, and purified by chromatography on an alumina column to afford 680 mg of coproporphyrin III, tetramethyl ester, as crystals.

EXAMPLE 4

*Arthrobacter hyalinus* (FERM-P No. 3125) was inoculated in a test tube, 21 mm in diameter, containing 15 ml of a sterilized culture medium containing per liter of deionized water, 10 ml of isopropyl alcohol, 1.0 g of yeast extract, 3.0 g of peptone, 3.0 g of ammonium sulfate, 0.4 g of monopotassium phosphate, 1.5 g of disodium phosphate, 5.0 g of magnesium sulfate, 10 ml of manganese sulfate, 10 mg of zinc sulfate, 200 $\mu$g of copper sulfate, 10 $\mu$g of molybdenum trioxide, 5.0 g of calcium carbonate and 0.2 g of L-cystine, and cultivated with shaking at 30° C. for 3 days. Isopropyl alcohol was added every 2 to 3 days thereafter, and 85 ml in total of isopropanol per liter of the culture broth was added over 17 days.

The concentration of coproporphyrin III accumulated in the culture broth at this time was 330 mg/liter.

EXAMPLE 5

The same cultivation as in Example 4 was carried out for 17 days except that the culture medium did not contain the L-cystine. The concentration of coproporphyrin III accumulated in the culture broth at this time was 230 mg/liter.

EXAMPLE 6

The same cultivation as in Example 4 was performed for 17 days except that the amount of magnesium sulfate in the culture medium was decreased to 0.5 g per liter of the culture medium. The concentration of coproporphyrin III accumulated in the culture broth at this time was 220 mg/liter.

COMPARATIVE EXAMPLE 2

The same cultivation as in Example 4 was carried out for 17 days except that the culture medium did not contain the L-cystine, and the amount of magnesium sulfate was decreased to 0.5 g. The concentration of coproporphyrin III accumulated in the culture broth was 150 mg/liter.

EXAMPLE 7

*Arthrobacter aurescens* (IFO 12136), *Arthrobacter pascens* (IFO 12139) and *Arthrobacter ramosus* (IFO 12958) were cultivated in the same way as in Example 1. The results are shown in Table 1.

TABLE 1

| Strain | Cultivation period | Amount of coproporphiyrin III produced (mg/liter) |
|---|---|---|
| *Arthrobacter aurescens* (IFO 12136) | 17 | 110 |
| *Arthrobacter pascens* (IFO 12139) | 15 | 210 |
| *Arthrobacter ramosus* (IFO 12958) | 15 | 82 |

EXAMPLE 8

The same cultivation as in Example 4 was carried out for 17 days except that 5-methyl-DL-tryptophan-resistant strain of *Arthrobacter hyalinus* (FERM-P NO. 5256) was used as the coproporphyrin III-producing microorganism. The concentration of coproporphyrin III accumulated in the culture broth at this time was 420 mg/liter.

EXAMPLE 9

The same cultivation as in Example 4 was carried out for 17 days except that coproporphyrin III-resistant strain (FERM-P No. 5259) of *Arthrobacter hyalinus* was used as the coproporphyrin III-producing microoganisms. The concentration of coproporphyrin III accumulated in the culture broth at this time was 450 mg/liter.

EXAMPLE 10

The same cultivation as in Example 1 was carried out for 15 days except that L-tryptophan-resistant strain (FERM-P No. 5258) of *Arthrobacter globiformis* was used as the coproporphyrin III-producing microorganism. The concentration of corpoporphyrin III accumulated in the culture broth at this time was 320 mg/liter.

EXAMPLE 11

The same cultivation as in Example 1 was carried out for 15 days except that L-tryptophan-resistant strain (FERM-P NO. 5257) of *Arthrobacter pascens* was used as the coproporphyrin III-producing microorganism. The concentration of coproporphyrin III accumulated in the culture broth at this time was 260 mg/liter.

EXAMPLE 12

Production of the 5-methyl-DL-tryptophan-resistant strain (FERM-P No. 5256) of *Arthrobacter hyalinus;*

*Arthrobacter hyalinus* (FERM-P No. 3125) was inoculated in a test tube (21 mm in outside diameter) containing 15 ml of the sterilized culture medium shown in Example 4 (to be referred to as the P medium), and cultivated with shaking at 30° C. for 3 days. The culture broth was put into a Petri dish, and subjected to ultraviolet irradiation for 2 minutes (two 15 W lamps located 40 cm above the Petri dish). The treated liquid was cultivated for 10 days in a test tube (21 mm in outside diameter) containing 15 ml of the sterilized P medium containing 5-methyl-DL-tryptophan. The culture broth was inoculated in a plate containing the P medium containing 5-methyl-DL-tryptophan and agar, and cultivated at 30° C. From the resulting colonies, that which had high ability to produce coproporphyrin III was separated as a 5-methyl-DL-tryptophan-resistant strain of *Arthrobacter hyalinus.*

EXAMPLE 13

Production of a coproporphyrin III-resistant strain (FERM-P No. 5259) of *Arthrobacter hyalinus:*

Example 12 was repeated except that coproporphyrin III was added to the culture medium instead of the 5-methyl-DL-tryptophan. From the colonies obtained, that which had high ability to produce coproporphyrin III was separated as a coproporphyrin III-resistant strain of *Arthrobacter hyalinus.*

EXAMPLE 14

Production of L-tryptophan-resistant strain (FERM-P No. 5258) *Arthrobacter globiformis:*

*Arthrobacter globiformis* (ATCC 8010) was inoculated in a test tube (21 mm in outside diameter) containing 15 ml of the sterilized culture medium shown in Example 1 (to be referred to as the G medium), and cultivated with shaking at 30° C. for 3 days. The culture broth was put into a Petri dish, and subjected to ultraviolet irradiation for 2 minutes (two 15 W lamps located 40 cm above the Petri dish). The treated liquid was cultivated for 10 days in a test tube (21 mm in outside diameter) containing 15 ml of the sterilized G medium containing L-tryptophan. The culture broth was inoculated in a plate containing the G medium containing L-tryptophan and agar, and cultivated at 30° C. From the colonies obtained, that which showed high ability to produce coproporphyrin III was separated as an L-tryptophan-resistant strain of *Arthrobacter globiformis.*

EXAMPLE 15

Production of L-tryptophan-resistant strain (FERM-P No. 5257) of *Arthrobacter pascens:*

Example 14 was repeated except that *Arthrobacter pascens* (IFO 12139) was used instead of the *Arthrobacter globiformis.* From the colonies obtained, that which showed high ability to produce coproporphyrin III was separated as an L-tryprophan-resistant strain of *Arthrobacter pascens.*

What we claim is:

1. In a process for producing coproporphyrin III which comprises cultivating a coproporphyrin III-producing microorganism of the genus Arthrobacter in a culture medium containing a carbon source, a nitrogen source and a mineral and recovering coproporphyrin III from the culture broth, the improvement wherein the culture medium contains at least 0.1 g, per liter of the culture medium, of L-cystine, at least 0.5 g, per liter of the culture medium, of $Mg^{++}$, or both.

2. The process of claim 1 wherein the amount of L-cystine is 0.1 to 5 g per liter of the culture broth, and the amount of $Mg^{++}$ is 0.5 to 10 g per liter of the culture medium.

3. The process of claim 1 wherein the cultivation is carried out at a temperature of about 20° C. to about 40° C. and a pH of about 4 to about 9.5.

4. The process of claim 1 wherein the microbial cells separated from the culture broth, or a crude enzyme extract from the microbial cells, is reacted with a coproporphyrin III-forming substrate, and coproporphyrin III is recovered from the reaction product.

5. The process of claim 1 wherein the coproporphyrin III-producing microorganism is *Arthrobacter hyalinus, Arthrobacter globiformis, Arthrobacter aurescens, Arthrobacter pascens, Arthrobacter ramosus, Arthrobacter cremeus, Arthrobacter resinosus, Artrobacter isopropanolophila, Arthrobacter flavidus* or a variety or mutant thereof.

6. The process of claim 5 wherein the copropor-phyrin III-producing microorganiusm is *Arthrobacter hyalinus* FERM-P No. 3125, *Arthrobacter hyalinus* ATCC 31263, *Arthrobacter hyalinus* DSM 867, Arthrobacter globiformis ATCC 8010, *Arthrobacter globiformis* IFO 12137, *Arthrobacter aurescens* ATCC 13344, *Arthrobacter aurescens* IFO 12136, *Arthrobacter pascens* ATCC 14358, *Arthrobacter pascens* IFO 12139, *Arthrobacter ramosus* ATCC 13727, *Arthorobacter ramosus,* IFO 12958, *Arthrobacter cremeus* FERM-P No. 3126, *Arthrobacter resinosus* FERM-P No. 3131, *Arthrobacter isopropanolophlila* FERM-P No. 3129, *Arthrobacter flavidus* FERM-P No. 3130, a 5-methyl-DL-tryptophan-resistant strain FERM-P No. 5256 of *Arthrobacter hyalinus,* a coproporphyrin III-resistant strain FERM-P No. 5259 of *Arthrobacter hyalinus,* an L-tryptophan-resistant strain FERM-P No. 5258 of *Arthrobacter globiformis,* or an L-tryptophan-resistant strain FERM-P No. 5257 of *Arthrobacter pascens.*

* * * * *